(12) United States Patent
McFadden

(10) Patent No.: US 9,078,657 B2
(45) Date of Patent: Jul. 14, 2015

(54) ANEURYSM CLIP

(71) Applicant: Joseph T McFadden, Norfolk, VA (US)

(72) Inventor: Joseph T McFadden, Norfolk, VA (US)

(*) Notice: Subject to any disclaimer, the term of this patent is extended or adjusted under 35 U.S.C. 154(b) by 186 days.

(21) Appl. No.: 13/795,362

(22) Filed: Mar. 12, 2013

(65) Prior Publication Data
US 2013/0267973 A1  Oct. 10, 2013

Related U.S. Application Data

(60) Provisional application No. 61/621,653, filed on Apr. 9, 2012.

(51) Int. Cl.
*A61B 17/08* (2006.01)
*A61B 17/12* (2006.01)
*A61B 17/122* (2006.01)

(52) U.S. Cl.
CPC ....... *A61B 17/12109* (2013.01); *A61B 17/1227* (2013.01); *A61B 17/12* (2013.01)

(58) Field of Classification Search
CPC .. A61B 17/12; A61B 17/122; A61B 17/1227; B42F 1/02; B42F 1/04; B42F 1/06; B42F 1/08; B42F 1/10
USPC ......... 606/120, 151, 157, 158, 213, 215, 216, 606/219, 220; 24/67.9, 533, 546, 547, 24/DIG. 10; D19/65
See application file for complete search history.

(56) References Cited

U.S. PATENT DOCUMENTS

| | | | | |
|---|---|---|---|---|
| 4,444,187 | A * | 4/1984 | Perlin | 606/158 |
| 5,683,405 | A * | 11/1997 | Yacoubian et al. | 606/158 |
| 7,322,995 | B2 * | 1/2008 | Buckman et al. | 606/157 |
| 2003/0229368 | A1 * | 12/2003 | Viola | 606/158 |
| 2007/0032806 | A1 * | 2/2007 | Qi et al. | 606/151 |

* cited by examiner

*Primary Examiner* — Jonathan W Miles
(74) *Attorney, Agent, or Firm* — Peter J. Van Bergen

(57) ABSTRACT

An aneurysm clip includes a compression spring having a compression axis, a first end, and a second end. A first force receiving surface is coupled to the first end of the spring, and a second force receiving surface is coupled to the second end of the spring. A first arm coupled to the first force receiving surface is approximately parallel to the spring's compression axis. A second arm coupled to the second force receiving surface is approximately parallel to the spring's compression axis. A first clamping leg coupled to the first arm extends approximately perpendicular therefrom, and a second clamping leg coupled to the second arm extends approximately perpendicular therefrom. The first and second clamping legs oppose one another and are biased into contact with one another by the spring.

9 Claims, 2 Drawing Sheets

ANEURYSM CLIP

Pursuant to 35 U.S.C. §119, the benefit of priority from provisional application 61/621,653, with a filing date of Apr. 9, 2012, is claimed for this non-provisional application.

FIELD OF THE INVENTION

The invention relates generally to aneurysm clips, and more particularly to an aneurysm clip that is compact and applies substantial and uniform pressure to an aneurysm's origin.

BACKGROUND OF THE INVENTION

An aneurysm is an unwanted widening or ballooning of some portion of an artery. This condition occurs when there is weakness in the artery wall. Some of the more common locations for an aneurysm include one of the major heart arteries, the brain, behind the knee, in the intestines, and in the spleen. While the causes of aneurysms and the symptoms associated therewith can vary, surgical treatment is typically required. During such surgery, it is generally necessary to place a spring-loaded clip across the origin of the aneurysm to prevent any more blood from entering the aneurysm and/or minimize the amount of blood leaking from the aneurysm should it rupture.

Conventional aneurysm clips involve some type of scissoring or clamping legs. A spring-loaded actuator coupled to the legs causes the legs to open for placement around the origin of the aneurysm and then close once the actuator is released. In order to prevent all blood flow, a substantial and uniform clamping force must be applied by the legs. Further, since there is frequently very little room for the aneurysm clip and since it remains in the patient, the design of the clip must be compact.

SUMMARY OF THE INVENTION

Accordingly, it is an object of the present invention to provide an aneurysm clip.

Another object of the present invention is to provide an aneurysm clip that produces a substantial and uniform clamping force for application to an aneurysm's origin.

Still another object of the present invention is to provide a compact aneurysm clip.

Other objects and advantages of the present invention will become more obvious hereinafter in the specification and drawings.

In accordance with the present invention, an aneurysm clip includes a compression spring having an axis of compression, a first end, and a second end. A first force receiving surface is coupled to the first end of the compression spring. A second force receiving surface is coupled to the second end of the compression spring. A first arm coupled to the first force receiving surface is approximately parallel to the compression axis of the compression spring. A second arm coupled to the second force receiving surface is approximately parallel to the compression axis of the compression spring. A first clamping leg coupled to the first arm extends approximately perpendicular therefrom. A second clamping leg coupled to the second arm extends approximately perpendicular therefrom. The first clamping leg and second clamping leg oppose one another and are biased into contact with one another by the compression spring.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
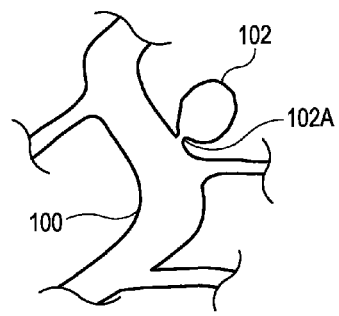
FIG. 1 is an isolated view of a portion of an artery with an aneurysm bulging from the wall thereof.

Referring now to the drawings and more particularly to FIG. 1, a portion of an artery 100 is illustrated with an aneurysm 102 formed along a wall of artery 100. The location and/or purpose of artery 100 are not limitations of the present invention. As is known in the art, aneurysm 102 is essentially a bulging or ballooning portion of the wall of artery 100. The origin 102A of aneurysm 102 allows blood (not shown) flowing through artery 100 to fill aneurysm 102. As aneurysm 102 grows, its walls become thinner and weaker. Absent treatment, aneurysm 102 will eventually leak or rupture. Surgery is generally the treatment of choice. During a surgical repair of an aneurysm, origin 102A is clamped using what is known in the art as an aneurysm clip.

Referring additionally and simultaneously to FIGS. 2-7, an aneurysm clip in accordance with an embodiment of the present invention is shown in a variety of views and is referenced generally by numeral 10. Aneurysm clip 10 is in its closed position in FIGS. 2-6, and in its open position in FIG. 7. In general, aneurysm clip 10 is a compact device that supports one-handed gripping and use by means of what is known in the art as a clip applier (not shown). The entirety of clip 10 can be an integrated device made from a single piece of material that provides the requisite spring force needed to cut off blood flow through origin 102A into aneurysm 102, while being acceptable for long-term placement in the human body. Such an integrated, one-piece aneurysm clip can be made from materials that include titanium, titanium alloys, alloys of chromium, nickel, cobalt and molybdenum (e.g., MP35N available from DuPont), alloys of chromium, nickel and cobalt, as well as materials that combine glasses and metals that are also referred to as metallic glasses or "glassimetals".

Figure 3:
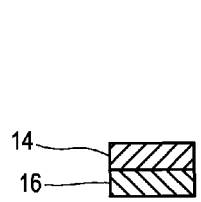
FIG. 3 is a cross-sectional view of the aneurysm clip's clamping legs taken along line 3-3 in FIG. 2.

Clip 10 includes a spring-loaded actuator portion referenced by numeral 12, and clamping legs 14 and 16 coupled to/integrated with actuator 12. When clip 10 is closed (i.e., no force is applied to actuator 12 as will be described further below), legs 14 and 16 are forced into an abutting relationship with one another (as shown) as opposing clamping forces $F_c$ are applied to legs 14 and 16 by actuator 12. The abutting surfaces of legs 14 and 16 are planar as shown in FIG. 3.

Spring actuator 12 includes opposing pressure plates 20 and 22 with a coil compression spring 24 disposed between and coupled/integrated on either end thereof to a respective one of plates 20 and 22. Spring 24 biases plates 20 and 22 away from one another. More specifically, the central axis of compression (indicated by dashed line 24A) of compression spring 24 passes through each of plates 20 and 22 in a nearly perpendicular relationship thereto. The pitch of the spring's coils defines an (acute) angular relationship between plates 20 and 22. The outward facing surfaces of plates 20 and 22 can be flat (as shown) and will generally include some structure (e.g., holes 20A and 22A) that allow a clip applier (not shown) to grip and operate clip 10 as would be understood in the art.

Figure 4:
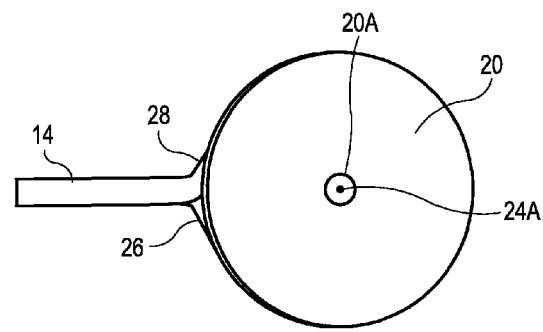
FIG. 4 is a plan view of the aneurysm clip taken along line 4-4 in FIG. 2.
Figure 5:
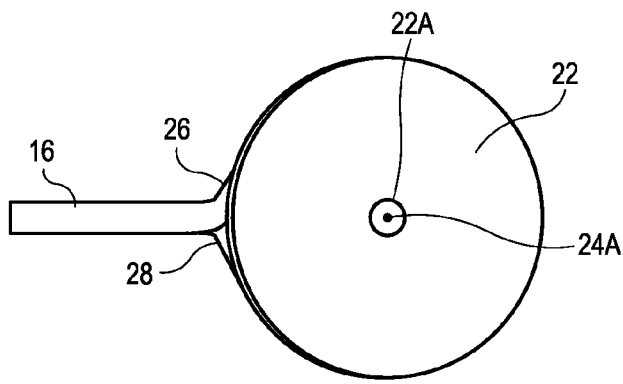
FIG. 5 is a plan view of the aneurysm clip taken along line 5-5 in FIG. 2.
Figure 6:
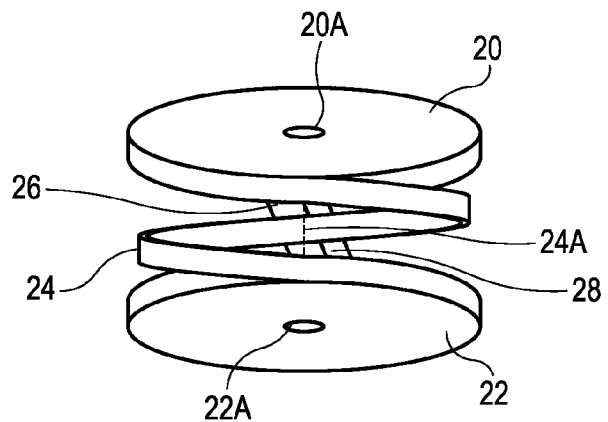
FIG. 6 is an end view of the aneurysm clip taken along line 6-6 in FIG. 2.

Plate 20 is coupled to/integrated with leg 16 via an extension arm 26 that is (i) approximately or substantially perpendicular to leg 16, and (ii) approximately or substantially parallel to compression axis 24A. In a similar fashion, plate 22 is coupled to/integrated with leg 14 via an extension arm 28 that is (i) approximately or substantially perpendicular to leg 14, and (ii) approximately or substantially parallel to compression axis 24A. Arms 26 and 28 are adjacent to spring 24. Legs 14 and 16 can be longitudinally aligned with compression axis 24A (as best seen in FIGS. 4 and 5) to provide a balanced feel when plates 20 and 22 are squeezed together during use of clip 10. Such alignment of legs 14 and 16 with compression axis 24A can be achieved by shaping one or both (as shown) of extension arms 26 and 28 prior to their integration with legs 16 and 14, respectively.

Figure 2:
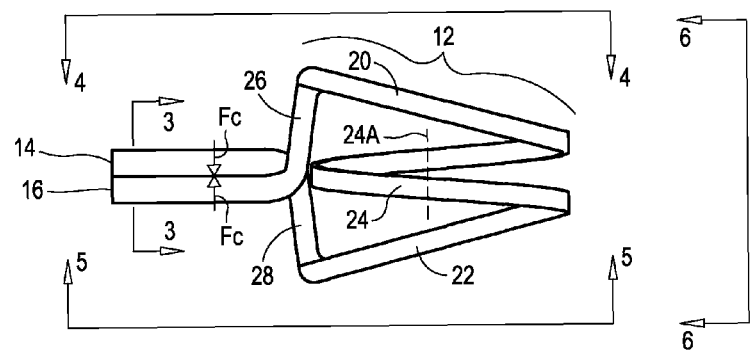
FIG. 2 is a side view of an aneurysm clip in the closed position in accordance with an embodiment of the present invention.
Figure 7:
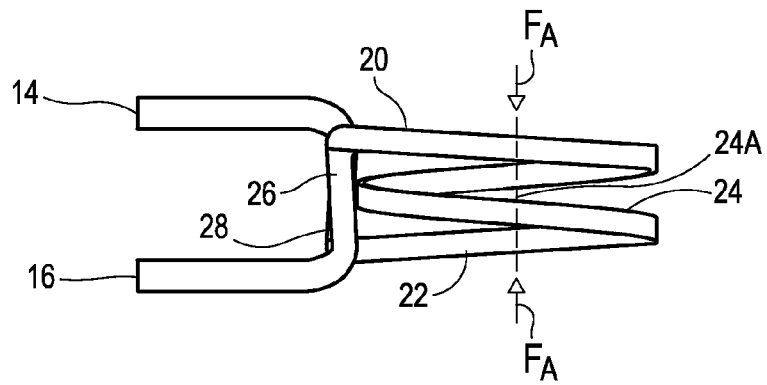
FIG. 7 is a side view of the aneurysm clip is its open position.

As mentioned above, plates 20 and 22 form the gripping place for a clip applier held by a surgeon. When a surgeon uses the clip applier to apply an actuating force $F_A$ to each of plates 20 and 22 as shown in FIG. 7, spring 24 is readily compressed along compression axis 24A as the nearly perpendicular relationship of plates 20/22 to compression axis 24A allows force $F_A$ to be nearly aligned with compression axis 24A. Since arms 26 and 28 are approximately parallel to compression axis 24A, nearly all of force $F_A$ is coupled to legs 16 and 14, respectively. Also, since legs 14 and 16 are approximately perpendicular to arms 28 and 26, respectively, legs 14 and 16 are forced away from one another in an approximate parallel fashion as arms 26 and 28 are driven in opposing directions aligned approximately parallel to axis 24A. Once the spaced-apart legs 14 and 16 are placed on either side of an aneurysm's origin (not shown in FIG. 7), the surgeon operates the clip applier to release clip 10 thereby removing actuating force $F_A$ so that clip 10 returns to its closed position with legs 14/16 clamped about an aneurysm's origin. The above-described orientation of compression axis 24A and arms 26/28 allow nearly all of the biasing force of compression spring 24 to form the clamping force $F_C$ (FIG. 2). Further, since legs 14/16 abut in planar faces and open/close while remaining approximately parallel to one another, the clamping force imparted thereby will be applied uniformly across an aneurysm's origin.

Plates 20 and 22 can be sized such that the peripheral edges thereof are approximately aligned with the diametric confines of spring 24. In this way, clip opening forces applied by a surgeon to plates 20 and 22 are readily distributed to spring 24. This also allows plates 20 and 22 to act as a shield for spring 24 to minimize the chances that foreign matter will get caught in spring 24.

The advantages of the present invention are numerous. A substantial and uniform clipping/clamping force is provided by a compression spring whose compression axis is aligned approximately perpendicular to the plates receiving an actuating force and aligned approximately parallel to the arms used to control the clipping/clamping legs. This structure provides for a short overall clip length thereby making it safer to use and safer to leave in a patient. The plates provide large force application surfaces, facilitate gripping of the clip, and shield the actuator's compression spring to prevent unwanted body portions from being captured in the spring's coils.

Although the invention has been described relative to a specific embodiment thereof, there are numerous variations and modifications that will be readily apparent to those skilled in the art in light of the above teachings. It is therefore to be understood that the invention may be practiced other than as specifically described.

What is claimed as new and desired to be secured by Letters Patent of the United States is:

1. An aneurysm clip, comprising:
   a single piece of material shaped to define
   a compression spring having a central axis of compression, a first end, and a second end;
   a first plate integrated with said first end of said compression spring;
   a second plate integrated with said second end of said compression spring;
   a first arm integrated with said first plate and adjacent to said compression spring, said first arm being approximately parallel to said central axis of said compression spring;
   a second arm integrated with said second plate and adjacent to said compression spring, said second arm being approximately parallel to said central axis of said compression spring;
   a first clamping leg coupled to said first arm and extending approximately perpendicular therefrom;
   a second clamping leg coupled to said second arm and extending approximately perpendicular therefrom; and
   said first clamping leg and said second clamping leg opposing one another and biased into an abutting relationship by said compression spring.

2. The aneurysm clip as in claim 1, further comprising a hole in a surface of each of said first plate and said second plate, each said hole being aligned with said central axis of said compression spring.

3. The aneurysm clip as in claim 1, wherein peripheral edges of each of said first plate and said second plate are approximately aligned with diametric confines of said compression spring.

4. The aneurysm clip as in claim 1, wherein said first clamping leg and said second clamping leg abut one another at planar surfaces thereof.

5. The aneurysm clip as in claim 1, wherein each of said first plate and said second plate is approximately perpendicular to said central axis of said compression spring.

6. The aneurysm clip as in claim 1, wherein said single piece of material is selected from the group consisting of (i) titanium, (ii) titanium alloys, (iii) alloys of chromium, nickel, cobalt and molybdenum, (iv) alloys of chromium, nickel and cobalt, and (v) metallic glasses.

7. An aneurysm clip, comprising:
   a single piece of material shaped to define
   a compression spring having a central axis of compression, a first end, and a second end;
   a first plate integrated with said first end of said compression spring;
   a second plate integrated with said second end of said compression spring;
   a hole in a surface of each of said first plate and said second plate, each said hole being aligned with said central axis of said compression spring;
   a first arm integrated with said first plate and adjacent to said compression spring, said first arm being approximately parallel to said central axis of said compression spring;

a second arm integrated with said second plate and adjacent to said compression spring, said second arm being approximately parallel to said central axis of said compression spring;

a first clamping leg coupled to said first arm and extending approximately perpendicular therefrom, said first clamping leg defining a first planar surface;

a second clamping leg coupled to said second arm and extending approximately perpendicular therefrom, said second clamping leg defining a second planar surface;

said first arm and said second arm positioning said first clamping leg and said second clamping leg in an opposing relationship with one another, wherein said first planar surface and said second planar surface oppose one another, and wherein said first planar surface is biased into an abutting relationship with said second planar surface by said compression spring; and said single piece of material selected from the group consisting of (i) titanium, (ii) titanium alloys, (iii) alloys of chromium, nickel, cobalt and molybdenum, (iv) alloys of chromium, nickel and cobalt, and (v) metallic glasses.

8. The aneurysm clip as in claim 7, wherein peripheral edges of each of said first plate and said second plate are approximately aligned with diametric confines of said compression spring.

9. The aneurysm clip as in claim 7, wherein each of said first plate and said second plate is approximately perpendicular to said central axis of said compression spring.

* * * * *